United States Patent [19]

Edwards

[11] Patent Number: 4,825,009

[45] Date of Patent: * Apr. 25, 1989

[54] PREPARATION OF NONIONIC SURFACTANTS

[75] Inventor: Charles L. Edwards, Houston, Tex.

[73] Assignee: Shell Oil Company, Houston, Tex.

[*] Notice: The portion of the term of this patent subsequent to Jan. 26, 2005 has been disclaimed.

[21] Appl. No.: 102,196

[22] Filed: Sep. 29, 1987

Related U.S. Application Data

[63] Continuation of Ser. No. 812,604, Dec. 23, 1985, Pat. No. 4,721,816.

[51] Int. Cl.$^4$ .............................................. C07C 41/03
[52] U.S. Cl. ..................................................... 568/618
[58] Field of Search ................................. 568/618, 620

[56] References Cited

U.S. PATENT DOCUMENTS 4,543,430 9/1985 Falgoux et al. ..................... 568/618

FOREIGN PATENT DOCUMENTS

71460/81 6/1984 Australia .
85/00365 1/1985 World Int. Prop. O. .

Primary Examiner—Howard T. Mars

[57] ABSTRACT

Alkylene oxide adducts of higher alkanols are prepared by a process which comprises contacting and reacting an alkylene oxide reactant comprising one or more $C_2$ to $C_4$ vicinal alkylene oxides with an alkanol reactant comprising one or more $C_6$ to $C_{30}$ alkanols in the presence of a catalytically effective amount of a catalyst which combines (i) one or more sulfur-containing acids with (ii) one or more aluminum compounds selected from the group consisting of aluminum alcoholates and aluminum phenolates, the relative molar ratio of component (i) to component (ii) being in the range from about 0.1:1 to 1:1. Alkanol alkoxylates, and particularly alkanol ethoxylates, prepared in this manner are characterized by a relatively narrow-range distribution of alkylene oxide adducts and by a relatively low content of residual alkanol. The products of this process are nonionic surfactants, particularly useful as components of detergent formulations.

18 Claims, No Drawings

PREPARATION OF NONIONIC SURFACTANTS

This is a continuation of application Ser. No. 812,604, filed Dec. 23, 1985 U.S. Pat. No. 4,721,816.

BACKGROUND OF THE INVENTION

This invention relates to the preparation of nonionic alkanol alkoxylates as the reaction products of alkylene oxides with detergentrange, i.e., $C_8$ to $C_{20}$, alkanols. More particularly, this invention is directed to a process for preparation of such surfactant materials utilizing an alkoxylation catalyst which combines an aluminum compound with a sulfur-containing acid.

A large variety of products useful, for instance, as nonionic surfactants, wetting and emulsifying agents, solvents, and chemical intermediates, are prepared by the addition reaction (alkoxylation reaction) of alkylene oxides with organic compounds having one or more active hydrogen atoms. As an example, particular mention may be made of the alkanol ethoxylates and alkyl-substituted phenol ethoxylates prepared by the reaction of ethylene oxide with aliphatic alcohols or substituted phenols of about 6 to 30 carbon atoms. Such ethoxylates, and to a lesser extent corresponding propoxylates and compounds containing mixed oxyethylene and oxypropylene groups, are most commonly applied as nonionic detergent components of commercial cleaning formulations for use in industry and in the home.

An illustration of the preparation of an alkanol ethoxylate (represented by formula III below) by addition of a number (n) of ethylene oxide molecules (formula II) to a single alkanol molecule (formula I) is presented by the equation

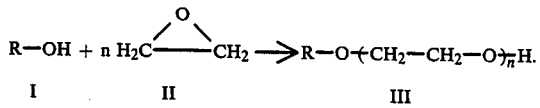

I II III

The addition of alkylene oxides to alkanols and other active-hydrogen containing compounds is known to be desirably promoted by a catalyst, most conventionally a catalyst of either strongly acidic or strongly basic character. Recognized in the art as suitable basic catalysts are the basic salts of the alkali metals of Group I of the Periodic Table, e.g., sodium, potassium, rubidium, and cesium, and the basic salts of certain of the alkaline earth metals of Group II of the Periodic Table, e.g., calcium, strontium, barium and in some cases magnesium. Conventional acidic alkoxylation catalysts include, broadly, the Lewis acid or Friedel-Crafts catalysts. Specific examples of these catalysts are the fluorides, chlorides, and bromides of boron, antimony, tungsten, iron, nickel, zinc, tin, aluminum, titanium and molybdenum. The use of complexes of such halides with, for example, alcohols, ethers, carboxylic acids, and amines have also been reported. Still other examples of known acidic alkoxylation catalyts are sulfuric and phosphoric acids; perchloric acid and the perchlorates of magnesium, calcium, manganese, nickel and zinc; metals oxalates, sulfates, phosphates, carboxylates and acetates; alkali metal fluoroborates, zinc titanate; and metal salts of benzene sulfonic acid.

In one important aspect, the present invention relates to an alkoxylation reaction catalyzed by a particular combination of one or more of certain aluminum compounds with a sulfur-containing acid such as sulfuric acid, sulfur trioxide, or a sulfonic acid. In another important aspect, the invention further involves the discovery of a process for the production of alkylene oxide adducts of alkanols (termed alkanol alkoxylates or simply alkoxylates for purposes of describing this invention) which are characterized by a narrow or peaked alkylene oxide adduct distribution. Alkylene oxide addition reactions are known to produce a product mixture of various alkoxylate molecules having different numbers of alkylene oxide adducts (oxyalkylene adducts), e.g., having different values for the adduct number n in formula III above. The adduct number is a factor which in many respects controls the properties of the alkoxylate molecule, and efforts are made to tailor the average adduct number of a product and/or the distribution of adduct numbers within a product to the product's intended service.

The present invention provides a process characterized by enhanced selectivity for the preparation of alkoxylate mixtures in which a relatively large proportion of the alkoxylate molecules have a number (n) of alkylene oxide adducts that is within a relatively narrow range of values. It has been reported that alkoxylate products having such a narrow range distribution are preferred for use in certain detergent formulations (Great Britain Pat. No. 1,462,134; Derwent Publications Research Disclosure No. 194,010). Narrow-range alkoxylates are also known to be particularly valuable as chemical intermediates in the synthesis of certain carboxyalkylated alkyl polyethers (U.S. Pat. No. 4,098,818) and of certain alkyl ether sulfates (Great Britain Pat. No. 1,553,561). Conventional commercial alkoxylate preparation, which has in large part been limited to the use of basic catalysts, particularly the metals sodium and potassium and their oxides and hydroxides, yields only a relatively broad distribution range product. Conventional acidcatalyzed alkoxylation reactions have long been known to produce a more narrow range product than that obtained with the alkali metal catalysts. Characteristic of the product of the typical acid-catalyzed alkoxylation is a statistical Poisson distribution in which the relative concentration of each individual alkoxylate species may be expressed in terms of the following equation, which is well known to those in the oligomerization and polymerization arts:

$$P(n) = \frac{N^n e^{-N}}{n!}$$

wherein N represents the overall molar ratio of reactant alkylene oxide to reactant alkanol, n represents alkylene oxide adduct number, P(n) represents the mole percent of alkoxylate product molecules having the adduct number n, and e indicates the natural logarithm function. In effect, this expression reflects a reaction mechanism under which all hydroxyl-containing species in the alkoxylation reaction mixture (i.e., both alkanol reactant and alkoxylate intermediates) react with the alkylene oxide at the same rate.

Although acid catalysis provides a relatively narrow distribution product, it is known to have substantial disadvantage in several other respects. For instance, the acids are often unstable with limited life and effectiveness as catalysts in the alkoxylation mixture. Both the acid catalysts themselves and their decomposition products catalyze side reactions producing relatively large amounts of polyalkylene glycols, and also react directly with the components of the alkoxylation mixture to yield undesirable, and often unacceptable, by-products such as organic derivatives of the acids. Overall, use of acid alkoxylation catalysts is known to result in relatively poor quality products.

Also of substantial importance in the alkoxylation of the higher ($C_6$ to $C_{30}$) alkanols is the ability of the process to minimize the quantity of unreacted (or residual) alkanol reactant remaining in the product. A high level of residual alkanol either represents a loss of valuable reactant, or requires that further processing of the product be carried out to recover the alcohol. Moreover, the presence of unreacted alkanol is recognized to be of disadvantage from the standpoint of product quality and environmental concerns. For instance, residual alkanol in the product contributes to volatile organic emissions during spray drying of detergent formulations.

It has recently been reported in the art that, in addition to conventional acidic catalysts, a number of other substances have been found to function as catalysts or in co-catalyst combinations which are capable of producing relatively narrow distributions for the oxyalkylene adducts of higher alkanols, and, in some cases, products having relatively low levels of residual alkanol reactant. For instance, it has recently been disclosed (U.S. Pat. Nos. 4,306,093 and 4,239,917, and published European Patent Application Nos. 0026544, 0026546, and 0026547) that certain compounds of barium, strontium, and calcium promote narrow-range alkoxylation products. U.S. Pat. Nos. 4,210,764 and 4,223,164 describe the use of cresylic acids to promote alkoxylation catalyzed by barium and strontium compounds. U.S. Pat. No. 4,302,613 reports that a more peaked reaction product can be obtained by combining barium and strontium alkoxylation catalysts with co-catalysts such as calcium oxide, calcium carbide, calcium hydroxide, magnesium metal, magnesium hydroxide, zinc oxide and aluminum metal. U.S. Pat. No. 4,453,023 describes a process for preparing alkoxylates having a narrower molecular weight distribution which employs a catalyst comprising a barium compound and a promoter selected from the class consisting of superphosphoric acid, phosphoric acid, diphosphoric acid, triphosphoric acid, phosphorous acid, dihydrogen phosphate compounds, oxides of phosphorous, carbon dioxide, and oxalic acid. U.S. Pat. No. 4,453,022 describes a similar process wherein the catalyst comprises a calcium or strontium compound and a promoter selected from the class consisting of superphosphoric acid, phosphoric acid, diphosphoric acid, triphosphoric acid, phosphorous acid, dihydrogen phosphate compounds, oxides of phosphorus, sulfuric acid, bisulfate compounds, carbonic acid, bicarbonate compounds, carbon dioxide, oxalic acid and oxalic acid salts, sulfur trioxide, sulfur dioxide, and sulfurous acid. U.S. Pat. No. 4,375,564 reports that a narrow range product results from alkoxylation reactions catalyzed by a magnesium compound in combination with a compound of one of the elements aluminum, boron, zinc, titanium, silicon, molybdenum, etc. U.S. Pat. No. 4,483,941 discloses catalysts for alkoxylation reactions which comprise either $BF_3$ or $SiF_4$ in combination with an alkyl or alkoxide compound of aluminum, gallium, indium, thallium, titanium, zirconium, and hafnium. U.S. Pat. No. 4,456,697 describes an alkoxylation catalyst which comprises a mixture of HF and one or more metal alkoxides. Japanese patent specification No. 52051307 to Tokuyama Soda KK discloses the selective preparation of mono- rather than di- or tri-alkylene glycol esters from alkylene oxide and alcohol using solid acid catalysts such as silica, alumina, titania, vanadium pentoxide, antimony pentoxide, titanyl sulfate, tungstic acid, phosphotungstic acid, and silver perchlorate.

SUMMARY OF THE INVENTION

It has now been found that certain combinations of (i) one or more sulfur-containing acids such as sulfuric acid, alkyl sulfuric acids, sulfur trioxide and sulfonic acids, and (ii) one or more soluble compounds of aluminum, are very effective as catalysts for the addition reaction of alkylene oxides and $C_6$ to $C_{30}$ alkanols, and are responsible for alkoxylate products which are characterized by both an exceptionally narrow-range distribution of alkylene oxide adducts and an exceptionally low residual alkanol content.

Accordingly, in the broad sense, the invention is a process for the preparation of alkoxylates of $C_6$ to $C_{30}$ alkanols which comprises contacting an alkylene oxide reactant comprising one or more lower (e.g., $C_2$ to $C_4$) vicinal alkylene oxides with an alkanol reactant comprising one or more $C_6$ to $C_{30}$ alkanols in the presence of a catalyst prepared by contacting (i) one or more of certain sulfur-containing acids and (ii) one or more aluminum alcoholate and/or aluminum phenolate compounds.

The sulfur-containing acid which is used as an alkoxylation process catalyst component or precursor for purposes of the invention is preferably one or more compounds selected from the group consisting of sulfur trioxide, sulfuric acid, alkyl sulfuric acids, and organic and inorganic sulfonic acids. The aluminum alcoholate and/or phenolate compounds can be applied per se, i.e., added directly to the process mixture, or, alternatively, can be formed in situ in the alcohol-containing process mixture by introduction of suitable precursors capable of conversion to aluminum alcoholate and/or phenolate compound(s), which in turn function as a catalyst component or as a precursor to the desired catalyst.

In comparison to conventional alkoxylation reactions carried out in the presence of conventional acidic catalysts alone, the process of the invention yields (1) a higher quality product relatively free of by-products, (2) a product having a narrower distribution of alkylene oxide adducts, and (3) a product having a reduced level of residual alkanol.

DESCRIPTION OF THE PREFERRED EMBODIMENTS

The present invention centers upon discoveries associated with the use in an alkoxylation process of a certain class of catalysts. Apart from the use of such catalysts, the process of the invention is, as a general rule, suitably conducted using such reactants and practicing under such processing procedures and reaction conditions as are known to the art for alkanol alkoxylation reactions. Certain preferences may, however, be expressed for particular reactants, procedures and conditions.

Thus, the invention is preferably applied to processes utilizing an alkylene oxide (epoxide) reactant which comprises one or more $C_2$ to $C_4$ vicinal alkylene oxides. Reactants which comprise ethylene oxide, propylene oxide, or mixtures of ethylene oxide and propylene oxide are preferred, while reactants wherein the alkylene oxide content consists essentially of ethylene oxide are considered particularly preferred.

The alkanol reactant very suitably comprises one or more alkanols having carbon number in the range from about 6 to 30. An alkanol reactant consisting essentially of primary, mono-hydric alkanols is considered most preferred, although secondary and tertiary alcohols as well as polyhydric alkanols are also very suitably utilized in the process of the invention either alone or in mixtures with the primary mono-hydric alkanols. Most preferably, the alkanol reactant consists essentially of one or more $C_6$ to $C_{30}$ primary mono-hydric alkanols. Preference can also be expressed for alkanols having from 8 to about 20 carbon atoms, with $C_9$ to $C_{18}$ alkanols considered more preferred and $C_{11}$ to $C_{16}$ alcohols considered most preferred. As a general rule, the carbon chains of the alkanols may be of either branched or linear (straight chain) structure, although preference further exists for alkanol reactants in which greater than about 50 percent, more preferably greater than about 70 percent and most preferably greater than about 90 percent of the molecules are of linear (straight-chain) carbon structure. In large part, such preferences relate more to the utility and value of the product alkoxylates in commercial services than to the operability or performance of the process of the invention.

The general suitability of such alkanols as reactants in alkoxylation reactions is well recognized in the art. Examples of specific alkanols and of commercially available alkanols and alkanol mixtures within this class are also well known and are recited in the aforementioned U.S. Patents and published patent applications, the relevant disclosures of which exemplifying such specific alkanols and alkanol mixtures are incorporated herein by this reference. Commercially available mixtures of primary mono-hydric alkanols prepared via the oligomerization of ethylene and the hydroformylation or oxidation and hydrolysis of the resulting higher olefins are particularly preferred. Examples of such commercially available alkanol mixtures include the NEODOL Alcohols, trademark of and sold by Shell Chemical Company, including mixtures of $C_9$, $C_{10}$ and $C_{11}$ alkanols (NEODOL 91), mixtures of $C_{12}$ and $C_{13}$ alkanols (NEODOL 23), mixtures of $C_{12}$, $C_{13}$, $C_{14}$, and $C_{15}$ alkanols (NEODOL 25), and mixtures of $C_{14}$ and $C_{15}$ alkanols (NEODOL 45); the ALFOL Alcohols, trademark of and sold by Continental Oil Co., including mixtures of $C_{10}$ and $C_{12}$ alkanols (ALFOL 1012), mixtures of $C_{12}$ and $C_{14}$ alkanols (ALFOL 1214), mixtures of $C_{16}$ and $C_{18}$ alkanols (ALFOL 1618), and mixtures of $C_{16}$, $C_{18}$ and $C_{20}$ alkanols (ALFOL 1620); the EPAL Alcohols, trademark of and sold by Ethyl Chemical Company, including mixtures of $C_{10}$ and $C_{12}$ alkanols (EPAL 1012), mixtures of $C_{12}$ and $C_{14}$ alkanols (EPAL 1214), and mixtures of $C_{14}$, $C_{16}$, and $C_{18}$ alkanols (EPAL 1418); and the TERGITOL-L Alcohols, trademark of and sold by Union Carbide Corporation, including mixtures of $C_{12}$, $C_{13}$, $C_{14}$, and $C_{15}$ alkanols (TERGITOL-L 125). Also very suitable are the commercially available alkanols prepared by the reduction of naturally occurring fatty esters, for example, the CO and TA products of Procter and Gamble Company and the TA alcohols of Ashland Oil Company.

For purposes of the invention, the alkylene oxide reactant and the active hydrogen reactant are necessarily contacted in the presence of the specified two-component catalyst.

As one component of this catalyst, the process of the invention makes use of one or more sulfur-containing acids. Particularly useful are sulfur trioxide ($SO_3$) and acids of the class represented by the empirical formula $ZSO_3H$. Included within this class are sulfuric acid (with Z in the formula representing -OH), monoalkyl esters of sulfuric acid which are also commonly called alkyl sulfuric acids (with Z representing an alkoxy group), sulfurous acid (wherein Z represents H), and sulfonic acids wherein Z represents a univalent inorganic atom or organic radical.

Preferred alkyl sulfuric acids include those with an alkoxy group of about 1 to 30 carbon atoms. Alkyl sulfuric acids having an alkoxy group of about 1 to 20 carbon atoms are more preferred, while those having an alkoxy group of about 8 to 20 carbon atoms are considered most preferred.

Specific examples of suitable inorganic sulfonic acids include chlorosulfonic acid (wherein Z is Cl), fluorosulfonic acid (wherein Z is F) and sulfamic acid (wherein Z is $NH_2$).

Suitable organic sulfonic acids include the alkane- and cycloalkane sulfonic acids, as well as arenesulfonic acids and heterocyclic sulfonic acids. Specific examples of the alkane sulfonic acids include methanesulfonic acid, ethanesulfonic acid, propanesulfonic acid, butanemethanesulfonic acid, pentanesulfonic acid, hexanesulfonic acid, dodecanesulfonic acid, hexadecanesulfonic acid, trifluoromethane sulfonic acid, sulfosuccinic acid, and cyclohexylsulfonic acid. Specific examples of arenesulfonic acids include benzenesulfonic acid, toluenesulfonic acid, styrene-(i.e., vinyl benzene) sulfonic acid, 5-sulfosalicylic acid, phenolsulfonic acid, and 1,6-naphthalene disulfonic acid. Specific examples of heterocyclic sulfonic acids include sulfanilic acid. Alkyl and aryl groups of the sulfonic acid molecule are suitably substituted with relatively inert organic and/or inorganic substituents. Examples of substituted organic sulfonic acids include 4-hydroxybenzoic acid, trifluoromethane sulfonic acid, isethionic acid, and taurine.

As is the case for the aluminum containing component of the catalyst, the sulfur-containing catalyst component is suitably introduced directly to the process mixture or formed therein upon addition to the mixture of precursors of the sulfur-containing acid(s). Mixtures of sulfur containing acids are very suitable.

A particularly preferred group of sulfur-containing acids is that which consists of sulfuric acid, sulfur trioxide, $C_1$ to $C_{30}$ alkyl sulfuric acids, sulfanilic acid, toluenesulfonic acid, styrenesulfonic acid, methanesulfonic acid, and 5-sulfosalicylic acid. A catalyst component selected from the group consisting of sulfuric acid, sulfur trioxide, and the $C_1$ to $C_{30}$ alkyl sulfuric acids is considered more preferred, and sulfuric acid is considered most preferred, for use in the invention from the standpoint of overall process performance and economics, and of product quality.

The second necessary component of the catalyst of the process of the invention suitably comprises one or more aluminum alcoholate or phenolate compounds. Preferably, this component comprises one or more alkoxide or phenoxide compounds of the formula

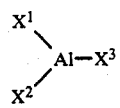

At least one of $X^1$, $X^2$, and $X^3$ represents an -OR moiety, wherein the R substituent is selected from the group consisting of alkyl and (optionally alkyl-substituted) phenyl moieties, preferably $C_1$ to $C_{30}$ alkyl and optionally substituted phenyl moieties. The $X^1$, $X^2$, and $X^3$ substituents which represent -OR groups suitably represent the same or different -OR groups. It is intended that the invention encompass embodiments utilizing aluminum compounds in which at least one of $X^1$, $X^2$ and $X^3$ represents a precursor moiety which undergoes conversion to an -OR moiety in the process mixture, and particularly in the presence of the alkanol reactant. Examples of such moieties which serve as precursors include halogen moieties, particularly chlorine and bromine atoms, carboxy (for instance acetate) groups, and alkyl (for instance methyl) groups. The one or more of $X^1$, $X^2$, and $X^3$ which are not either -OR groups or precursors for the formation of -OR groups suitably represent organic or inorganic moieities which are substantially inert in the process medium. Most preferably, $X^1$ and $X^2$ and $X^3$ all represent (or are in practice converted to) the same or different -OR groups.

Specific examples of preferred alkoxide compounds suitable as catalyst components for purposes of the invention include the aluminum alkoxides (wherein R is $C_1$ to $C_{30}$ alkyl), including the lower alkoxides, e.g., aluminum ethoxide, aluminum isopropoxide, and aluminum t-butoxide, as well as the higher alkoxides having one or more of their alkyl R substituents in the same $C_8$ to $C_{20}$ range as the alkanol reactant of the process, e.g., nonyl, decyl, dodecyl, and hexadecyl groups. Specific examples of preferred phenoxide compounds useful in this service include aluminum phenoxide, lower alkyl-substituted phenol derivatives such as aluminum benzyloxide and and higher alkyl-substituted phenol derivatives, e.g., compounds wherein R represents nonylphenyl, tridecylphenyl, pentadecylphenyl, etc. Specific examples of preferred compounds which serve as precursors for the formation in situ of aluminum alkoxide compounds include aluminum triacetate and trialkylaluminum compounds such as trimethylaluminum and triethylaluminum.

Particular preference exists for the use of an alkoxide in which each of the $X^1$, $X^2$, and $X^3$ substituents is an -OR group wherein R is an alkyl group having a carbon number in the range from 1 to about 30, more preferably a carbon number in the range from about 1 to 20, and most preferably a carbon number which corresponds to the carbon number(s) of the particular alkanol reactant employed in the given process application. Thus, for instance, the reaction of a dodecyl alcohol reactant is most preferably conducted in the presence of a catalyst which comprises a catalyst in which a substantial portion of the second catalyst component is a compound of the formula Al—(OR)$_3$, wherein each R is a dodecyl group. Without intention that the invention be limited to one theory or mechanism of- operation, it is thought that the alcoholate and phenolate compounds commonly undergo transalcoholysis reactions in the presence of the alkanol reactant and are converted, at least in part, to alkoxides having alkyl substituents of carbon numbers which correspond to those of the alkanol reactant. Thus, for example, when an aluminum isopropoxide catalyst component is contacted with a higher alkanol alkoxylation reactant (e.g., a $C_{12}$ to $C_{15}$ alkanol mixture) a transalcoholysis reaction results which liberates isopropanol and converts at least a portion of the aluminum isopropoxide to aluminum alkoxides having $C_{11}$ to $C_{15}$ alkyl substituents. In one preerred embodiment of the invention, a lower carbon number aluminum alkoxide (e.g., an alkoxide characterized by alkyl group carbon number(s) of less than about 6) is mixed with the alkanol reactant, prior to contact with the alkylene oxide reactant, under conditions which favor the conversion by transalcoholysis of the lower alkoxide compounds to alkoxide compounds which correspond in carbon number (or carbon number distribution) of the alkoxide substituent to the carbon number (or carbon number distribution) of the alkanol reactant.

In the practice of the process of the invention, the catalyst components are preferably applied in a molar ratio of the first sulfurcontaining acid component to the second aluminum containing component that is in the range from about 0.1:1 to 2:1. Higher relative ratios result in lower reaction rates and higher degrees of by-product formation, while at lower ratios the reaction rate is undesirably low. Molar ratios of the first catalyst component to its second component in the range from about 0.3:1 to 1:1 are more preferred, while molar ratios between about 0.4:1 and 0.6:1 are considered most preferred.

The catalyst combination is present in the reaction mixture in a catalytically effective amount. For the typical practical operation, a quantity of catalyst is desirably at least about 0.01% w (percent by weight) of the combined total of the two components relative to the alkanol reactant. Although catalyst quantity is not narrowly critical, preference may be expressed for use of the catalyst in amount of at least about 0.05% w, while an amount between about 0.1 and 1% w is considered most preferred. Substantially greater quantities of catalyst, e.g., up to about 10% w, are also very suitable.

In terms of processing procedures, the alkoxylation reaction in the invention may be conducted in a generally conventional manner. For example, the catalyst components may initially be mixed with the alkanol reactant. A substantially liquid mixture forms, although it is not necessary that all of the added catalyst dissolve in the alkanol. This mixture is then contacted, preferably under agitation, with alkylene oxide reactant, which is typically introduced in gaseous form.

The order in which the catalyst components and the reactants are contacted has not been found to be critically important to the invention. Thus, for instance, it is suitable practice to premix the aluminum compound catalyst component with the sulfur-containing component, prior to their introduction into contact with the alkanol reactant. The observation of a reaction between the two catalyst components when they are pre-mixed in the absence of alcohol and ethylene oxide suggests that the two specified components may in fact serve as precursors of a single effective catalyst which has not been otherwise identified. Accordingly, the catalyst is described with reference to a combination of, or, equivalently, to a catalyst prepared by contacting the two specified compo- nents.

Also very suitable, and generally preferred from the standpoint of convenience, is a combination of the two components by contact in the presence of the alkanol reactant, e.g., by independent, addition of the two components to the reactant.

It is considered surprising that such mixing or premixing of the two components results in an active catalyst for the alkoxylation reaction, in view of observations that aluminum sulfate salt is not effective as a catalyst for the desired reaction.

Overall, the two reactants are utilized in quantities which are predetermined to yield an alkoxylate product of the desired mean or average adduct number, e.g., typically from less than one to about 30. In general terms, suitable and preferred process temperatures and pressures for purposes of this invention are the same as in conventional alkoxylation reactions, between th same reactants, employing conventional catalysts. A temperature of at least about 70° C., particularly at least about 100° C., is typically preferred for a significant rate of reaction, while a temperature less than about 200° C., particularly less than about 180° C., and most particularly less than about 170° C., is typically desirable to minimize degradation of the product. The two-component catalyst used in the invention is highly active, and care must be taken to control the temperature of the exothermic reaction. Superatmospheric pressures, e.g., pressures between about 10 and 150 psig, are preferred. While these procedures describe a batch mode of operation, the invention is equally applicable to a continuous process.

The alkanol reactant is generally a liquid and the alkylene oxide reactant is generally a vapor for such reactions. Alkoxylation is then suitably conducted by introducing gaseous alkylene oxide into a pressure reactor containing the liquid alkanol and the two components of the catalyst combination. For considerations of process safety, the partial pressure of the lower alkylene oxide reactant is preferably limited, for instance, to less than about 60 psia, and/or the reactant is preferably diluted with an inert gas such as nitrogen, for instance, to a vapor phase concentration of about 50 percent or less. The reaction can, however, be safely accomplished at greater alkylene oxide concentration, greater total pressure and greater partial pressure- of alkylene oxide if suitable precautions, known to the art, are taken to manage the risks of explosion. A total pressure of between about 40 and 110 psig, with an alkylene oxide partial pressure between about 15 and 60 psig, is particularly preferred, while a total pressure of between about 50 and 90 psig, with an alkylene oxide partial pressure between about 20 and 50 psig, is considered more preferred.

After the ethoxylation reaction has been completed, the product is preferably neutralized to deactivate the catalyst. Neutralization is suitably accomplished by the addition of a base such as sodium or potassium hydroxide to the acidic product mixture. Neutralized catalyst residues are very suitably left in the product, or may be removed if desired, for example, by precipitation or extraction or the like.

The alkoxylate prepared in the process of the invention is typically a product of very acceptable quality, having a relatively low content of polyalkylene glycols and other by-products, as well as a low content of residual alkanol reactant. Although the content of residual alkanol will vary from one alkoxylation product to another, and is dependent upon the degree of alkoxylation, i.e., the average alkylene oxide adduct number, the residual alkanol content of a product prepared according to the invention and having a given average adduct number is less than than the content of residual alkanol in a product of like average adduct number which has been prepared according to conventional acid-catalyzed alkoxylation.

The following Examples and Comparative Experiments are provided to further illustrate certain specific aspects of the invention but are not intended to limit its broader scope.

Except as noted otherwise, each of the Examples and Comparative Experiments were conducted under the following procedure. All alkoxylation reactions were conducted in a one-liter stainless steel autoclave reactor. In each case, the alkylene oxide reactant consisted of ethylene oxide and the alkanol reactant was a NEODOL 23 Alcohol (trademark of Shell Chemical Company) characterized as a mixture of primary, 80% linear (20% branched) alkanols having twelve and thirteen carbon atoms (about 40% by mole $C_{12}$ and 60% by mole $C_{13}$). Initially, the liquid alkanol reactant was dried to a water content of about 40 ppm (as indicated by Karl Fischer water analysis) by sparging with nitrogen at 130° C. for one hour. About 2.0 grams (0.01 moles) of the first (aluminum compound) catalyst component was dissolved in about 150 grams (0.773 moles) of the dried alkanol in a multineck glass round-bottom flask at 100° C. The reaction mixture was cooled to about 30° C. at which point about 0.5 grams (0.005 moles) of the second (sulfur-containing acid) component was dissolved in the alkanol solution, producing a clear, colorless solution. This solution was transferred to the autoclave under a nitrogen atmosphere, and the reactor sealed and heated to 120° C. A mixture of nitrogen and ethylene oxide was then introduced into the reactor to a total pressure of 75 psia (45 psia nitrogen and 30 psia ethylene oxide). Alkoxylation (ethoxylation) commenced immediately. Temperature of the exothermic reaction mixture was allowed to rise to 140° C. and cooling was then applied to the reactor to maintain that temperature. Ethylene oxide was added to the reactor on demand, that is, at a rate necessary to maintain approximately constant pressure. Sufficient ethylene oxide was added to the reactor to produce a product having the desired average ethylene oxide adduct number. Ethylene oxide introduction was then discontinued and the reactor was maintained at 140° C. for an additional hour, to substantially consume unreacted ethylene oxide in the system. At the end of this hour, the reactor was cooled to 90° C., and the product was transferred under nitrogen atmosphere to a sample bottle and neutralized with base (i.e., potassium hydroxide) to a pH of about 6.5. The product was analyzed by GC-LC techniques to determine the mean average adduct number of the ethoxylate, the ethylene oxide adduct distribution of the ethoxylate, the content of residual alkanol reactant in the product, and the quantity of polyethylene glycol by-products formed.

EXAMPLE 1

Example 1 followed the general procedures outlined above, utilizing aluminum isopropoxide (Al(OR)$_3$, where R is isopropyl) as the first catalyst component and concentrated (96%) sulfuric acid as the second catalyst component. For purposes of the alkoxylation, 75 grams (2.2 moles) of ethylene oxide was added to the autoclave over a period of 30 minutes.

The alkanol ethoxylate product was found to have a mean average adduct number of 2.0 and to contain 4.4% w of residual alkanol reactant. The product also contained 0.6% w polyethylene glycols (PEG).

The ethylene oxide adduct distribution of the product is presented in Table I and compared with that of (1) an ethoxylate of equivalent mean adduct number which was produced using a conventional potassium hydroxide catalyst and (2) with a (calculated) Poisson distribution as is characteristic of conventional acid-catalyzed ethoxylation reactions. The distribution is substantially more narrow than that which is characteristic of conventional base-catalyzed ethoxylation reactions, including those catalyzed by compounds of sodium or potassium or other Group I metals as well as those catalyzed by compounds of barium or other Group II metals. Moreover, the distribution is more narrow than that obtained using conventional acid catalysts such as sulfuric acid.

TABLE I

Comparative Ethoxylate Distributions

| | Catalyst System | | |
|---|---|---|---|
| | KOH | (Poisson) | AL(OR)$_3$/H$_2$SO$_4$ |
| | Mean Average Adduct No. | | |
| Adduct Number | 2.0 | 2.0 | 2.0 |
| 0 (Residual Alcohol) | 24.5% w | 9.3% w | 4.5% w |
| 1 | 15.5 | 22.9 | 27.4 |
| 2 | 15.7 | 27.1 | 33.0 |
| 3 | 13.1 | 20.9 | 18.0 |
| 4 | 9.5 | 11.9 | 11.2 |
| 5 | 6.6 | 5.3 | 4.3 |
| 6 | 4.6 | 2.0 | 1.5 |
| 7 | 3.0 | 0.6 | |
| 8 | 2.0 | 0.2 | |
| 9 | 1.5 | | |
| 10 | 1.1 | | |
| 11 | 0.8 | | |
| 12 | 0.6 | | |
| 13 | 0.6 | | |
| 14 | 0.5 | | |
| 15 | 0.3 | | |

EXAMPLE 2

For Example 2, the general procedures were again followed as in Example 1, with the addition of separate processing step for the conversion of substantially all of the aluminum isopropoxide to an aluminum alkoxide of the C$_{12}$ and C$_{13}$ alkanols. After the addition of the second (sulfuric acid) catalyst component to the 150 grams of the dried alkanol reactant, and before the transfer of the alkanol/catalyst mixture to the autoclave, the mixture was heated to 130° C. and maintained at this temperature under a nitrogen sparge for two hours. Under these conditions, a transalcoholysis reaction occurred between the aluminum isopropoxide and the C$_{12}$ and C$_{13}$ alkanols. Isopropanol released by alcoholysis was removed from the system by the nitrogen sparge. Following the transalcoholysis, the mixture was cooled to 30° C. and transferred to the autoclave under nitrogen atmosphere.

A total of 76 grams of ethylene oxide was added to the reactor during the ethoxylation reaction, over a period of 60 minutes. The product was determined to have a mean average adduct number of 2.4, and to contain 3.1% w residual alcohol and 0.5% PEG. Ethylene oxide adduct distribution was also determined and is presented in the Table II, together with a comparative Poisson distribution.

TABLE II

| | Catalyst System | |
|---|---|---|
| | (Poisson) | AL(OR)$_3$/H$_2$SO$_4$ |
| | Mean Average Adduct No. | |
| Adduct Number | 2.5 | 2.4 |
| 0 (Residual Alcohol) | 5.3% w | 3.1% w |
| 1 | 16.1 | 19.4 |
| 2 | 23.8 | 27.6 |
| 3 | 22.9 | 23.8 |
| 4 | 16.3 | 14.6 |
| 5 | 9.1 | 6.9 |
| 6 | 4.2 | 2.7 |
| 7 | 1.6 | 1.6 |
| 8 | 0.6 | 0.2 |
| 9 | 0.2 | |

EXAMPLE 3

An alkoxylation process according to the invention was carried out using aluminum t-butoxide (Al(OR)$_3$, where R is t-butyl) as the first catalyst component. In this Example 3, about 5.0 grams (0.02 moles) of aluminum t-butoxide was dissolved in about 300 grams (1.55 moles) of the dried alkanol reactant at 100° C. The mixture was cooled to 30° C. and about 1.0 gram (0.01 moles) of concentrated sulfuric acid was added, producing a slightly hazy, colorless solution. The general procedure was then again followed for the ethoxylation reaction.

A total of 150 grams of ethylene oxide was consumed over a 90 minute reaction at 140° C. Analysis of the neutralized product indicated an alkoxylate with a mean average adduct number of 2.1, containing 4.5% w residual alkanol and 1.8% w PEG. The ethylene oxide distribution of the product was similar to that obtained in Example I.

EXAMPLE 4

An alkoxylation process according to the invention was conducted using a catalyst which contained the two catalyst components in a molar ratio of 1:1, i.e., one part of the first component (aluminum isopropoxide) and one part of the second component (concentrated sulfuric acid). For this purpose, about 1.1 grams (0.005 moles) of the first component was dissolved in 150 grams of the predried alkanol reactant at 100° C. The mixture was then cooled to 30° C., and about 0.5 grams (0.005 moles) of the sulfuric acid was added.

A total of about 70 grams of ethylene oxide was consumed over a period of 120 minutes. The product had a mean average adduct number of 2.0, and contained 4.4% w residual alkanol and 2.1% w PEG.

EXAMPLE 5

For Example 5, sulfur trioxide was utilized as the second catalyst component. About 2.7 grams (0.013 moles of aluminum isopropoxide was dissolved in the 150 grams of alkanol reactant at 100° C. The mixture was cooled to 30° C., and 1.06 grams (0.013 moles) of sulfur trioxide was added.

A total of 75 grams of ethylene oxide was consumed over a 30 minute ethoxylation reaction. Alkoxylate product had a mean average adduct number of 2.3, and contained 5.0% w residual alkanol and 1.1% w polyethylene glycol.

EXAMPLE 6

Another alkoxylation process according to the invention was carried out, in this case using p-toluenesulfonic acid as the second catalyst component. About 3.3 grams (0.02 moles) of p-toluene sulfonic acid monohydrate was added to 150 grams (0.773 moles) of predried alkanol reactant and the mixture further dried for 30 minutes under nitrogen sparge at 130° C. About 2.0 grams (0.01 moles) of aluminum isopropoxide was then added to the mixture and the resulting solution was nitrogen sparged at 130° C. for an additional 30 minutes to remove isopropanol released by transalcoholysis reaction.

Ethoxylation was conducted at 170° C. A total of 75 grams of ethylene oxide were consumed over a period of 90 minutes. The product was analyzed to have a mean average adduct number of 1.9 and to contain 7.5% w residual alcohol and 2.5% w PEG.

EXAMPLE 7

An alkoxylation process according to the invention was carried out using a catalyst containing components which had been pre-mixed, prior to the introduction of the catalyst into the alkanol reactant. For this purpose, 1.0 gram (0.01 mole) of 95% by weight sulfuric acid was added slowly to 4.93 grams (0.02 moles) of aluminum sec-butoxide (Al(OR)$_3$, where R is sec-butyl) at room temperature. An exothermic reaction commenced and the mixture was stirred at 95° C. for one hour, producing a light-pink semi-solid product. The mixture was then stirred for an additional 16 hours at 25° C.

The pre-mixed catalyst was added at 40° C. to 300 grams of the pre-dried alkanol reactant. The resulting mixture was heated to 100° C. to dissolve the catalyst and then transferred to the autoclave reactor. The ethoxylation reaction was then conducted in the specified manner, with 116 grams of ethylene oxide consumed over a 100 minute period. Analysis of the product after neutralization indicated a mean average adduct number of 1.7. The product contained 8.6% w alcohol and 1.0% w polyethylene glycol. The ethoxylate distribution of the product prepared under this Example is presented in Table III, which also illustrates for comparison the distribution obtained for a product of conventional acid (boron trifluoride) catalyzed reaction. The product of this Example had a significantly narrower distribution than those of conventional practices.

TABLE III

| | Catalyst System | |
|---|---|---|
| | BF$_3$ | AL(OR)$_3$/H$_2$SO$_4$ |
| Adduct Number | Average Adduct No. | |
| | 1.7 | 1.7 |
| 0 (Residual Alcohol) | 13.2% W | 8.6% w |
| 1 | 27.5 | 34.9 |
| 2 | 27.7 | 30.6 |
| 3 | 18.1 | 16.8 |
| 4 | 8.8 | 6.5 |
| 5 | 3.3 | 1.9 |
| 6 | 1.0 | 0.4 |
| 7 | 0.3 | 0.2 |

COMPARATIVE EXPERIMENT A

An alkoxylation process was conducted under the general procedures outlined above, but in the absence of the first catalyst component, and thus not in accordance with the invention. The only catalyst employed in this experiment was a sulfur-containing acid, in particular, sulfuric acid.

About 0.5 grams (0.005 moles) of sulfuric acid was dissolved in 150 grams (0.773 mole) of predried alkanol at 30° C. (No aluminum compound was added to this mixture.) The solution was transferred to the reactor and contacted with ethylene oxide under the general procedures. No reaction was observed at 140° C. As the reactor temperature was slowly increased, alkoxylation commenced at about 160° C. to 170° C. About 57 grams of ethylene oxide was consumed over a four hour period. The product had a mean average adduct number of about 1.0 and was found to contain 5.8% w PEG and a substantial quantity of other by-products which were not identified. The nature and quantity of the by-products did not permit determination of the ethoxylate distribution.

COMPARATIVE EXPERIMENT B

An alkoxylation process was conducted under the same procedures, but in the absence of the second catalyst component. In other words, the process was carried out in the presence of aluminum isopropoxide, but in the absence of a sulfur-containing acid.

About 1.0 gram (0.005 mole) of aluminum isopropoxide was mixed with 68 grams (0.35 mole) of the dried alkanol reactant. The mixture was sparged with nitrogen for 30 minutes at 130° C. and then transferred to a 300 milliliter stainless autoclave reactor and heated to 170° C. ethylene oxide and nitrogen were charged to the reactor to bring the total pressure to 85 psia (55 psia nitrogen and 30 psia ethylene oxide). ethoxylation commenced, but was extremely slow—only 12.3 grams of ethylene oxide were consumed over a five hour period. Analysis of the product indicated the formation of an alkoxide with a mean average adduct number of 0.9 and a residual alkanol content of 37.4 % w.

COMPARATIVE EXPERIMENT C

Comparative Experiment C illustrates that aluminum sulfate is not effective as an alkoxylation catalyst. A total of 0.58 grams of aluminum sulfate and 150 grams (0.773 mole) of the dried alkanol reactant were mixed in the autoclave reactor. The mixture was heated to 130° C. and then contacted with ethylene oxide under a total pressure of 75 psia (45 psia nitrogen and 30 psia ethylene oxide). No reaction occurred under these conditions. The temperature of the mixture was increased slowly to 170° C. and maintained at that temperature with stirring for a total of four hours. No ethylene oxide was consumed, and the alkanol reactant was recovered unchanged.

COMPARATIVE EXPERIMENT B

An alkoxylation process was conducted under the same general procedures, but in the absence of the second catalyst component. In other words, the process was carried out in the presence of aluminum isopropoxide, but in the absence of a sulfur-containing acid.

About 1.0 gram (0.005 mole) of aluminum isopropoxide was mixed with 68 grams (0.35 mole) of the dried alkanol reactant. The mixture was sparged with nitrogen for 30 minutes at 130° C. and then transferred to a 300 milliliter stainless autoclave reactor and heated to 170° C. Ethylene oxide and nitrogen were charged to the reactor to bring the total pressure to 85 psia (55 psia nitrogen and 30 psia ethylene oxide). Ethoxylation commenced, but was extremely slow—only 12.3 grams of ethylene oxide were consumed over a five hour period. Analysis of the product indicated the formation of an alkoxide with a mean average adduct number of 0.9 and a residual alkanol content of 37.4 % w.

COMPARATIVE EXPERIMENT C

Comparative Experiment C illustrates that aluminum sulfate is not effective as an alkoxylation catalyst. A total of 0.58 grams of aluminum sulfate and 150 grams (0.773 mole) of the dried alkanol reactant were mixed in the autoclave reactor. The mixture was heated to 130° C. and then contacted with ethylene oxide under a total pressure of 75 psia (45 psia nitrogen and 30 psia ethylene oxide). No reaction occurred under these conditions. The temperature of the mixture was increased slowly to 170° C. and maintained at that temperature with stirring for a total of four hours. No ethylene oxide was consumed, and the alkanol reactant was recovered unchanged.

I claim as my invention:

1. A process for the preparation of an alkanol alkoxylate product characterized by a narrow-range alkylene oxide adduct distribution and by a low content of residual alkanol, which comprises contacting and reacting an alkylene oxide reactant comprising one or more $C_2$ to $C_4$ vicinal alkylene oxides with an alkanol reactant comprising one or more $C_6$ to $C_{30}$ alkanols in the presence of a catalytically effective amount of a catalyst prepared by contacting (i) one or more sulfur-containing acids and (ii) one or more aluminum compounds selected from the group consisting of aluminum alcoholates and aluminum phenolates, the molar ratio of (i) to (ii) being in the range from about 0.1:1 to 2:1.

2. The process of claim 1, wherein the alkylene oxide reactant consists essentially of ethylene oxide and the alkanol reactant consists essentia-lly of one or more $C_6$ to $C_{30}$ primary mono-hydric alkanols.

3. The process of claim 2, wherein the one or more sulfurcontaining acids are selected from the group consisting of sulfur trioxide, sulfuric acid, alkyl sulfuric acids, sulfurous acid, and organic and inorganic sulfonic acids.

4. The process of claim 3, wherein the one or more sulfur-containing acids are selected from the group consisting of sulfuric acid, sulfur trioxide, $C_1$ to $C_{30}$ alkyl sulfuric acids, sulfanilic acid, toluenesulfonic acid, styrenesulfonic acid, methanesulfonic acid, and 5-sulfosalicylic acid.

5. The process of claim 2, wherein the one or more aluminum compounds have the formula

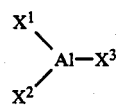

wherein at least one of $X^1$, $X^2$, and $X^3$ represents an -OR moiety, wherein R is selected from the group consisting of $C_1$ to $C_{30}$ alkyl, phenyl and alkyl substituted phenyl moieties.

6. The process of claim 5, wherein at least one of $X^1$, $X^2$, and $X^3$ represents an -OR moiety, wherein R is $C_1$ to $C_{30}$ alkyl 7. The process of claim 5, wherein each of $X^1$, $X^2$, and $X^3$ represents an -OR moiety wherein R is an alkyl group having a carbon number in the range from 1 to about 30.

8. The process of claim 3, wherein the one or more aluminum compounds have the formula

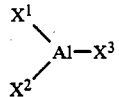

wherein at least one of $X^1$, $X^2$, and $X^3$ represents an -OR moiety, wherein R is selected from the group consisting of $C_1$ to $C_{30}$ alkyl, phenyl and alkyl substituted phenyl moieties.

9. The process of claim 8, wherein at least one of $X^1$, $X^2$, and $X^3$ represents an -OR moiety, wherein R is $C_1$ to $C_{30}$ alkyl 10. The process of claim 9, wherein each of $X^1$, $X^2$, and $X^3$ represents an -OR moiety wherein R is an alkyl group having a carbon number in the range from 1 to about 30.

11. The process of claim 4, wherein the one or more aluminum compounds have the formula

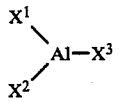

wherein at least one of $X^1$, $X^2$, and $X^3$ represents an -OR moiety, wherein R is $C_1$ to $C_{30}$ alkyl.

12. The process of claim 11, wherein each of $X^1$, $X^2$, and $X^3$ represents an -OR moiety wherein R is an alkyl group having a carbon number in the range from 1 to about 30.

13. The process of claim 2 wherein the molar ratio of (i) to (ii) is in the range from about 0.3:1 to 1:1.

14. The process of claim 5 wherein the molar ratio of (i) to (ii) is in the range from about 0.3:1 to 1:1.

15. The process of claim 8 wherein the molar ratio of (i) to (ii) is in the range from about 0.3:1 to 1:1.

16. A process for the preparation of an alkanol ethoxylate product characterized by a narrow-range ethylene oxide adduct distribution and by a low constent of residual alkanol, which comprises contacting and reacting an alkylene oxide reactant consisting essentially of ethylene oxide with an alkanol reactant consisting essentially of one or more $C_8$ to $C_{20}$ primary monohydric alkanols in the presence of a catalytically effective amount of a catalyst prepared by contacting (i) one or more sulfur containing acids selected from the group consisting of sulfuric acid, sulfur trioxide, $C_1$ to $C_{30}$ alkyl sulfuric acids, sulfanilic acid, toluenesulfonic acid, styrenesulfonic acid, methanesulfonic acid, and 5-sulfosalicylic acid, and (ii) one or more aluminum compounds of the formula

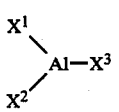

wherein at least one of $X^1$, $X^2$, and $X^3$ represents an -OR moiety, wherein R is selected from the group consisting of $C_1$ to $C_{30}$ alkyl, phenyl and alkyl substituted phenyl moieties, the molar ratio of (i) to (ii) being in the range from about 0.3:1 to 1:1.

17. The process of claim 16, wherein at least one of $X^1$, $X^2$, and $X^3$ represents an -OR moiety, wherein R is $C_1$ to $C_{30}$ alkyl.

18. The process of claim 16, wherein each of $X^1$, $X^2$, and $X^3$ represents an -OR moiety wherein R is an alkyl group having a carbon number in the range from 1 to about 30.

* * * * *